(12) United States Patent
Childers et al.

(10) Patent No.: US 7,776,559 B2
(45) Date of Patent: Aug. 17, 2010

(54) DISPOSABLE BLOOD TEST DEVICE (75) Inventors: Winthrop D. Childers, San Diego, CA (US); David Tyvoll, La Jolla, CA (US)

(73) Assignee: Hewlett-Packard Development Company, L.P., Houston, TX (US)

( * ) Notice: Subject to any disclaimer, the term of this patent is extended or adjusted under 35 U.S.C. 154(b) by 1686 days.

(21) Appl. No.: 10/762,784

(22) Filed: Jan. 22, 2004

(65) Prior Publication Data
US 2005/0163657 A1 Jul. 28, 2005

(51) Int. Cl.
*G01N 33/567* (2006.01)
(52) U.S. Cl. .................... 435/7.21; 435/7.24; 435/7.25; 435/174; 435/283.1; 435/287.1; 436/518; 436/149; 429/92
(58) Field of Classification Search .................. 422/50, 422/68.1, 82.01, 98; 435/4, 287.1, 287.9
See application file for complete search history.

(56) References Cited

U.S. PATENT DOCUMENTS

| 4,654,127 A | | 3/1987 | Baker et al. |
| 5,096,669 A | | 3/1992 | Lauks et al. |
| 5,182,707 A | | 1/1993 | Cooper et al. |
| 5,410,504 A | * | 4/1995 | Ward .......................... 365/149 |
| 5,695,623 A | | 12/1997 | Michel et al. |
| 5,872,713 A | | 2/1999 | Douglas et al. |
| 5,989,917 A | | 11/1999 | McAleer et al. |
| 6,168,957 B1 | | 1/2001 | Matzinger et al. |
| 6,175,752 B1 | | 1/2001 | Say et al. |
| 6,217,744 B1 | | 4/2001 | Crosby |
| 6,295,506 B1 | | 9/2001 | Heinonen et al. |
| 6,413,213 B1 | | 7/2002 | Essenpreis et al. |
| 6,600,997 B2 | | 7/2003 | Deweese et al. |
| 6,814,844 B2 | * | 11/2004 | Bhullar et al. .......... 204/403.01 |
| 2002/0006673 A1 | * | 1/2002 | Mandecki .................... 436/518 |
| 2003/0191415 A1 | | 10/2003 | Moerman et al. |
| 2003/0203498 A1 | | 10/2003 | Neel et al. |
| 2003/0204313 A1 | | 10/2003 | Ou-Yang et al. |
| 2004/0029109 A1 | * | 2/2004 | Lai ................................. 435/5 |
| 2005/0019953 A1 | * | 1/2005 | Groll ........................... 436/514 |
| 2008/0098802 A1 | * | 5/2008 | Burke et al. ............... 73/61.61 |

FOREIGN PATENT DOCUMENTS

GB 2 332 943 A 7/1999
WO WO 2004/113915 12/2004

OTHER PUBLICATIONS i-STAT, Product Info-Cartridges, 6 pages, <www.istat.com/products/cartridges.asp>, 2001.
i-STAT, Microfluidic and Biosensor Chip Technology, 3 pages, <www.istat.com/products/docs/biosenso.pdf>, last available 2002.

* cited by examiner

*Primary Examiner*—Nelson Yang (57) ABSTRACT

A disposable blood test device comprises a substrate configured for carrying a chemical reagent and circuitry formed on the substrate. The circuitry comprises a sensor portion associated with the chemical reagent to enable measurement of at least one of a presence and a concentration of a blood analyte, and an information storage portion configured to store information indicative of a property of the chemical reagent.

13 Claims, 7 Drawing Sheets

DISPOSABLE BLOOD TEST DEVICE

BACKGROUND

Millions of people across the globe face the daily challenge of managing their diabetes. Several times a day, they must test their blood for glucose levels. Currently, most consumers monitor their daily glucose levels by themselves through the use of electrochemical glucose meters. In these devices, a sample of blood is collected from a pin prick in the body into a test strip, which is inserted into a meter for calculation and display of the glucose level. The longevity and health of diabetics is directly related to how tightly their glucose levels are controlled through daily self-testing and administration of insulin, as well as diet and exercise. Accordingly, highly accurate glucose testing in self-monitoring can aid millions of diabetics who daily endeavor to maintain optimal blood glucose levels.

Moreover, since blood is a vital component of the body, many other blood analytes are of significant interest in managing human health. Accordingly, self-testing or measuring other analytes or properties of blood are also of interest as the medical industry seeks rapid and effective methods to monitor various medical conditions.

Disposable test strips used in self-testing must be calibrated to the meter with which they are used. In particular, these test strips include several chemical reagents for reaction with the blood sample to enable detection of a particular blood analyte. Since each set of test strips has a slightly different chemical composition, each set of test strips must be calibrated relative to the meter into which the test strips are inserted. Unfortunately, conventional calibration mechanisms do not provide a robust method for reliable and accurate calibration of test strips with meters.

DETAILED DESCRIPTION

In the following detailed description, reference is made to the accompanying drawings which form a part hereof, and in which is shown by way of illustration specific embodiments in which the invention may be practiced. In this regard, directional terminology, such as "top," "bottom," "front," "back," "leading," "trailing," etc., is used with reference to the orientation of the Figure(s) being described. Because components of embodiments of the present invention can be positioned in a number of different orientations, the directional terminology is used for purposes of illustration and is in no way limiting. It is to be understood that other embodiments may be utilized and structural or logical changes may be made without departing from the scope of the present invention. The following detailed description, therefore, is not to be taken in a limiting sense, and the scope of the present invention is defined by the appended claims.

Embodiments of the present invention are directed to a method for analyzing blood to detect an analyte or to determine a property of the blood. An analyte is any substance within a blood sample that is selected for detection. One blood analyte that can be measured indirectly through an electrochemical test includes glucose. In these tests, a sample of blood is exposed within a test strip to enzyme reagents for reaction with the glucose in the blood sample. The reaction products from the interaction of the blood glucose with the enzymes further interact with mediators and electrode sensors within the test strip as part of an electrochemical reaction. Based upon a measurement of current or charge at the electrode sensors from that electrochemical reaction, an indirect measurement of glucose concentration in the blood sample is obtained. Alternatively, the reaction products of the glucose-enzyme interaction are measured through reflectance photometry to indirectly determine a glucose level.

Embodiments of the present invention are directed to automatically calibrating disposable analyte test devices relative to a meter in which the test devices are inserted. Each disposable test device comprises calibration information that is electronically stored in the test device so that the calibration information is inseparable from the test device and electrically communicated to the meter, without any additional steps by the user, upon insertion into the meter. The calibration information comprises, but is not limited to, a value indicative of a property of a chemical reagent on the test device.

In one embodiment of the present invention, a disposable test device enables measuring a blood analyte. The test device comprises a substrate, circuitry, and a chemical reagent. The substrate carries the chemical reagent and is configured for receiving a blood sample. The circuitry is formed on the substrate and comprises a sensor portion and an information storage portion. The sensor portion is associated with a chemical reagent to enable measurement of a blood analyte in the blood sample. The information storage portion is configured to store calibration information about a property of the test device.

These properties of the test device may include, but are not limited to, information indicative of a property of the chemical reagent, a date of manufacture, and/or optimal operating electrical characteristics for the sensor portion, etc. For example, in some embodiments, a property of the test device (that is stored as part of the calibration information) can comprise a physical or electrical property of the test device, such as a geometry, sizes, and/or spacing of sensor electrodes on the test device.

Embodiments of the present invention can be applied for detection or measurement of many blood analytes other than glucose. Other common analytes of interest include, for example, markers for cardiovascular disease, drugs, illicit drugs, antibiotics, and antigens and toxins associated with infectious organisms. These analytes include, but are not limited to, troponins, b-type natriuretic peptide, clostridium difficile toxins, digitoxin, digoxin, theophylline, warfarin, barbiturates, methadone, amphetamine and amphetamine analogues, propoxyphene, opiates, cocaine, tetrahydrocannabinol, benzodiazepines, phencyclidine, gentamicin, vancomycin, acetyl choline, amylase, bilirubin, cholesterol, chorionic gonadotropin, creatine kinase, creatine, RNA, DNA, fructosamine, glutamine, hormones, ketones, lactate, peroxide, prostate-specific antigen, prothrombin, thyroid stimulating hormone, and their metabolites. U.S. Pat. No. 6,281,006 discloses methods to determine the concentration of RNA and DNA.

Figure 1:
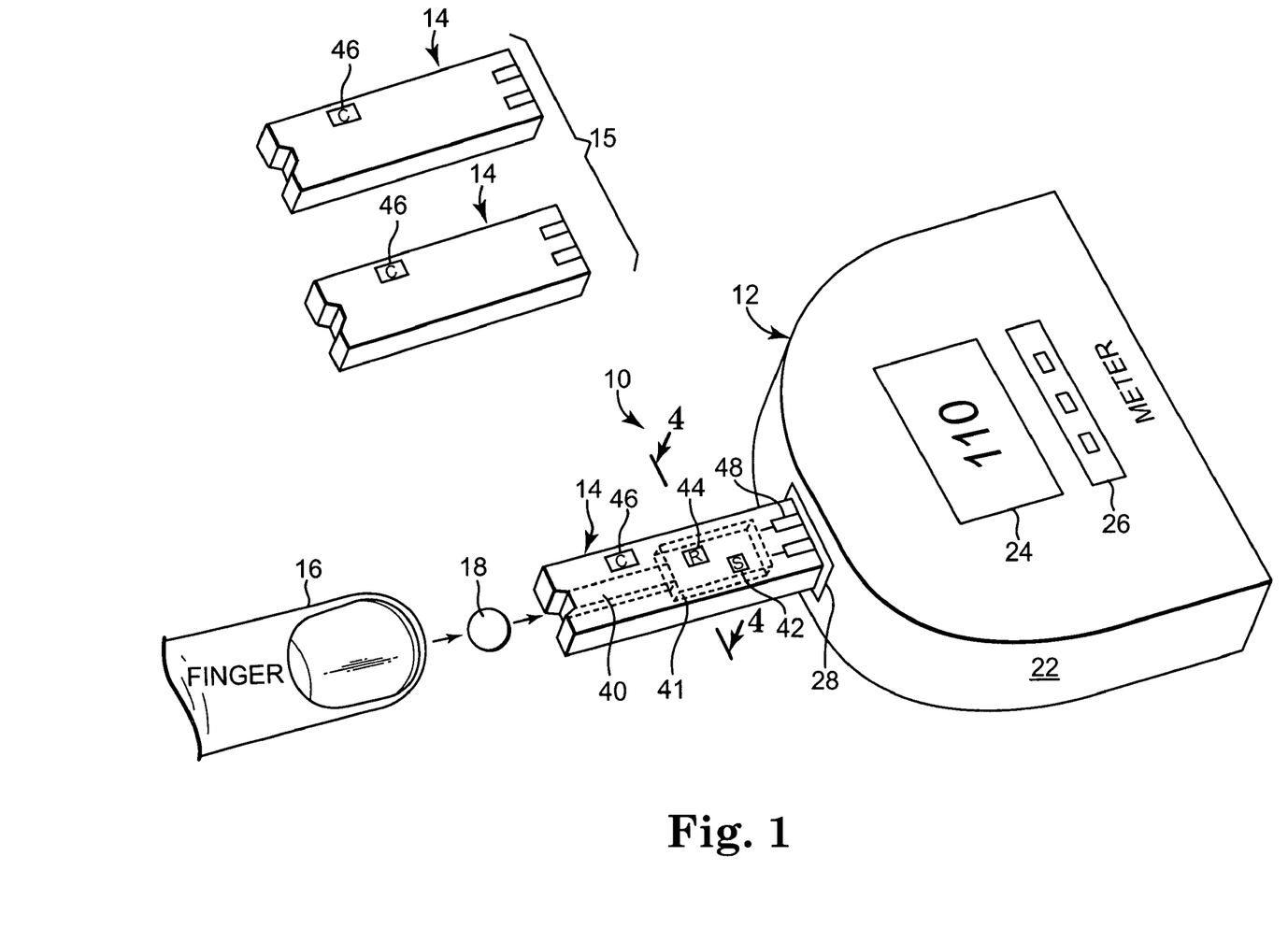
FIG. 1 is an isometric view of a blood analyzer system, according to an embodiment of the present invention.

In one embodiment shown in FIG. 1, system 10 is directed to testing blood properties, such as blood glucose levels, in blood sample 18 taken from a finger 16 or other body part of a human subject. System 10 comprises meter or receiving portion 12 and test device 14 (e.g., a test strip). Meter 12 is generally a handheld-type glucose meter used by patients to assist in self-monitoring their glucose levels. However, meter 12 is not precluded from being used to measure and monitor other analytes and properties of blood obtained and detected via a test strip. Moreover, meter 12 also can comprise a countertop testing device rather than a handheld device.

Test device 14 is removably insertable into a portion of meter 12 and is part of a set 15 of test devices 14. Each test device 14 comprises fluid pathway 40, chamber 41, sensor (S) 42, reagent (R) 44, calibration information (C) 46, and input/output contacts 48.

Test device 14 receives blood sample 18 via fluid pathway 40, which pulls blood sample 18 into chamber 41 via capillary fluid action through a combination of the fluid properties of blood and the dimensions, shape, and surface properties of pathway 40. Chamber 41 comprises a test surface with one or more enzyme or immunoassay reagents (R) 44 suitable for causing a chemical reaction or immunorecognition with an analyte in blood sample 18. This interaction creates a reaction product to enable indirect measurement of a blood analyte via an electrochemical or immunorecognition detection method. Calibration information (C) 46 represents one or more parameters affecting the performance of test device 14 with meter 12. For example, calibration information (C) 46 corresponds to one or more properties of test device 14, such as a calibration characteristic of the reagents (R) 44, a date of manufacture, meter operating characteristics with test device 14 (e.g., frequency, voltage, etc.), and/or sensor electrode characteristics (e.g., geometry, size, spacing, etc.).

Sensor 42 of test device 14 is disposed within chamber 41 and is configured as an electrode arrangement for applying an electrochemical test to determine a property of the blood, such as a blood glucose level. Finally, input/output contacts 48 of test strip 18 are electrically connected to sensor 42 and are exposed on a surface of test device 14 to be removably insertable within receiver 28 of meter 12 for establishing electrical communication between test device 14 and meter 12.

Meter 12 comprises housing 22, display 24, control panel 26, and receiver 28. Meter 12 includes housing 22 for enclosing system electronics to operate meter 12 and for supporting display 24 and control panel 26. Control panel 26 enables control of various functions of meter 12 directed at performing a test and/or evaluating results of a test on blood sample 18 performed within test device 14, including calibration of each test device 14 used with meter 12. Display 24 provides a graphical representation of the test results and related information to the test consumer. For example, display 24 can display information related to calibration of test device 14 with meter 12. Various aspects of meter 12, including system electronics carried therein, will be described in further detail in association with FIG. 2.

Figure 2:
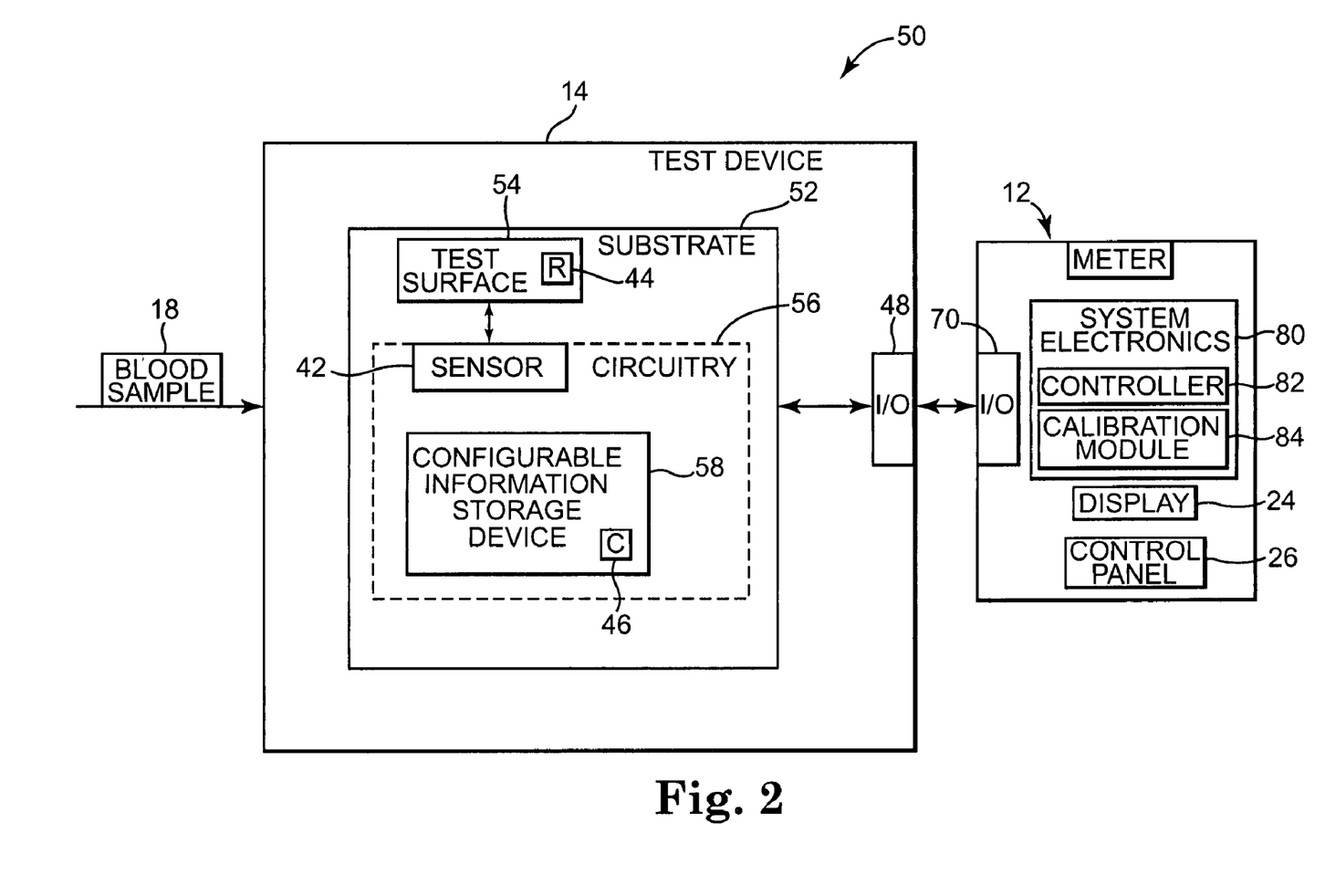
FIG. 2 is a schematic illustration of a blood analyzer system, according to an embodiment of the present invention.

FIG. 2 is a schematic illustration of a system 50 which functionally represents system 10. As shown in FIG. 2, system 50 comprises test device 14, including substrate 52, and meter 12. Substrate 52 of test device 14 comprises test surface 54 with reagent (R) 44, and circuitry 56. Circuitry 56 comprises sensor 42 and configurable information storage device 58 with calibration information 46.

As shown in FIG. 2, meter 12 comprises input/output contacts 70, system electronics 80, which includes among other components, controller 82 and calibration module 84. Controller 82 directs various functions of meter 12 including operation of display 24 and control panel 26, while cooperating with calibration module 84 to calibrate each test device 14 relative to meter 12.

Test surface 54 of test device 14 is defined by one or more walls of chamber 41 (FIG. 1) of test device 14 and carries reagents (R) 44 for electrochemical interaction with sensor 42. Information storage device 58 of test device 14 stores calibration information (C) 46 for test device 14, and in one embodiment, comprises one or more electrically conductive elements formed on substrate 52. In one embodiment, calibration information 46 comprises a value indicative of a property of one or more chemical reagents on test device 14. In some embodiments (such as those described in association with FIG. 8), information storage device 58 of test device 14 comprises a non-volatile memory portion and is configured to receive an electrical signal to store calibration information 46 including, but not limited to, a value of a property of chemical reagent(s), as well as additional information such as date of manufacture, operating characteristics, electrode characteristics, etc.

Information storage device 58 is formed, altered, programmed, and/or configured near the time of manufacture of test device 14 to store calibration information 46 pertinent for the test strip on which information storage device 58 resides. Since calibration information 46 for each test device is present on test device 14, the calibration information can never be separated from the test device(s) 14 as each test device 14 carries its own calibration information. Upon test device 14 being removably inserted into meter 12, calibration information 46 is automatically communicated from test device 14 to calibration module 84 of meter 12. This communication sets meter 12 to operate with appropriate calibration information 46 unique to test device 14 for achieving an accurate analyte test in blood-sample 18 (FIG. 1).

Figure 3:
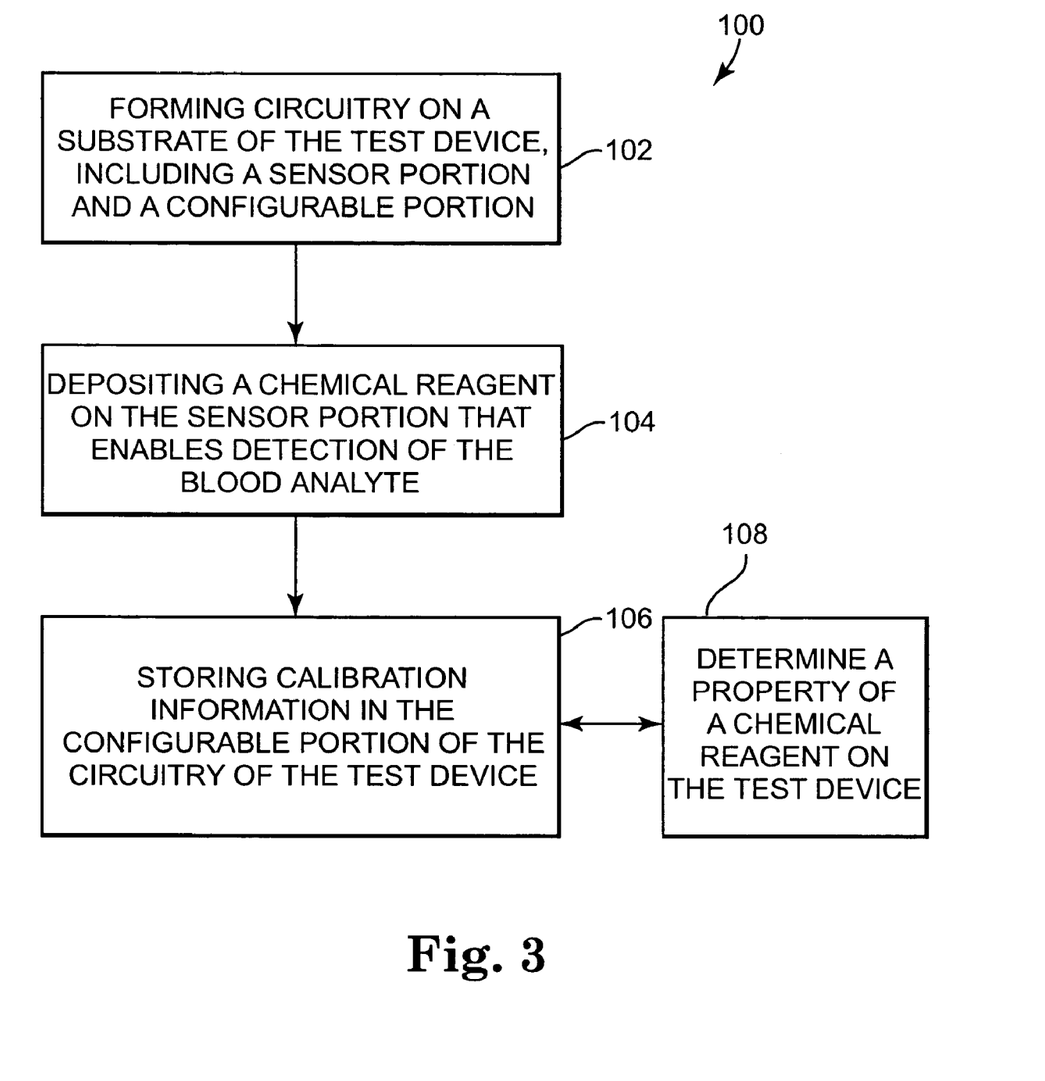
FIG. 3 is block diagram of a method of manufacturing a test strip, according to an embodiment of the present invention.

As shown in FIG. 3, method 100 is directed to manufacturing a self-calibrating test device. The systems, or combinations of systems of FIGS. 1-2 and 4-8 are suitable for performing method 100.

As shown in box 102 of FIG. 3, method 100 comprises forming circuitry on a substrate of a test device with the circuitry including a sensor portion and a configurable portion. In one embodiment, the circuitry is made by depositing metallization traces over a flexible substrate to form the sensors and configurable information storage device. This embodiment is further described and illustrated in association with FIGS. 4-7.

In one embodiment, all of the circuitry formed on the test device is formed in-situ during the fabrication of the test device. In other words, the circuitry is formed or deposited directly onto the substrate through one or more processes such as vapor or plasma deposition, plasma-enhanced vapor deposition, lamination, etching, photolithography, electroplating, diffusion, or the like. In addition other processes can be performed to modify the circuitry. For example, a laser process can be used to modify and enhance properties of amorphous silicon.

In some embodiments, the circuitry is made using semiconductor micro-fabricating techniques including some of those techniques listed above in which a thin film transistor portion of the circuitry comprises or couples to a non-volatile memory portion defining the configurable information storage device for storing calibration information. This embodiment is further described and illustrated in association with FIG. 8.

As shown in box 104, method 100 further comprises depositing on the substrate a chemical reagent of the sensor portion that enables detection of the blood sample. In one embodiment, these chemical reagent(s) comprise a chemical reagent that is activated upon contact of blood sample 18 with the reagents.

As shown in box 106, another aspect of method 100 comprises storing calibration information in the configurable portion of the circuitry of the test device. Another aspect of method 100, as shown in box 108, comprises determining a property of a chemical reagent on the test device for storage as all of, or part of, calibration information into configurable portion of the circuitry of the test device.

Figure 4:
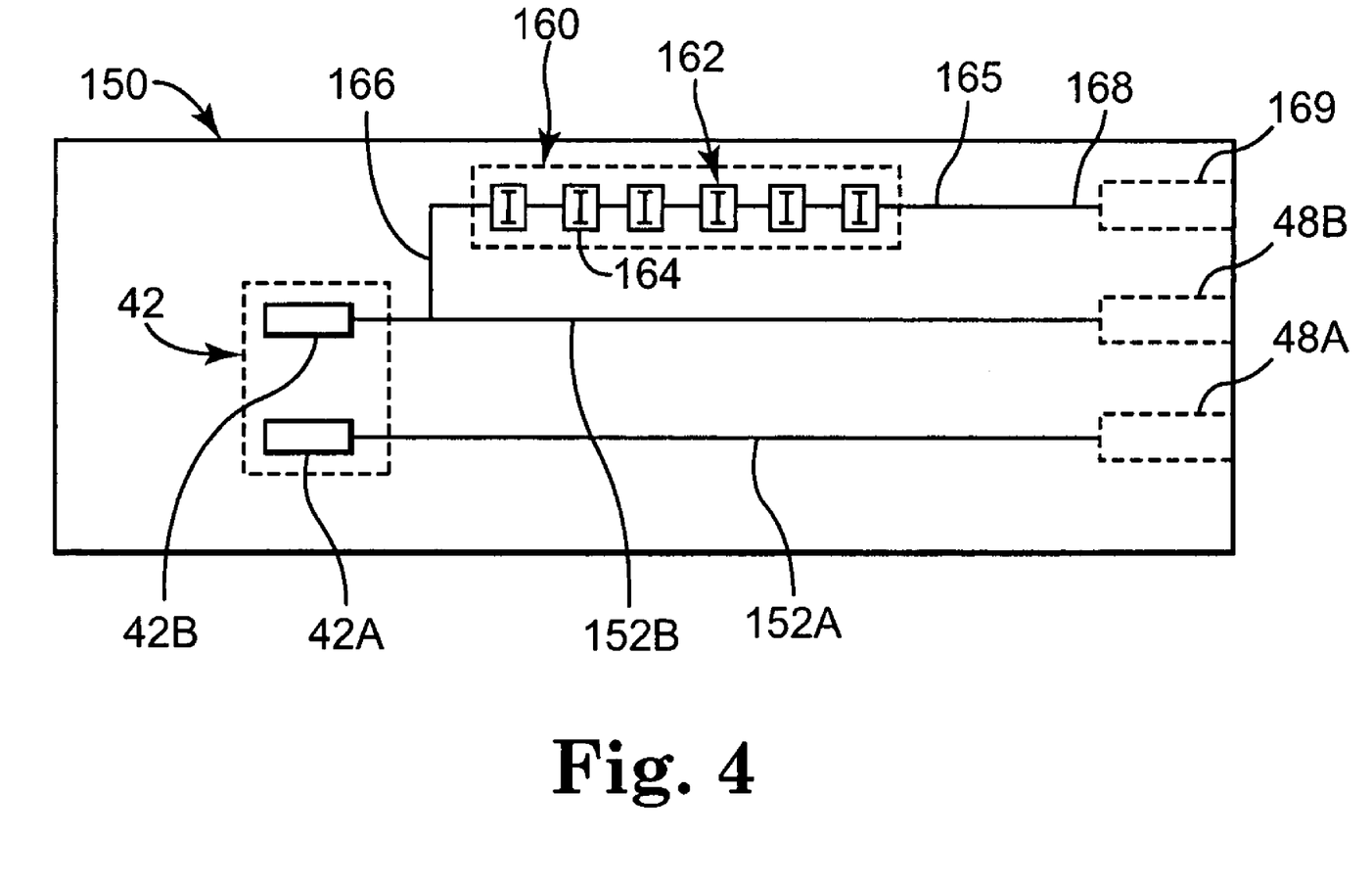
FIG. 4 is a top plan view of a test strip, according to an embodiment of the present invention.

One embodiment of a test device is shown in FIG. 4. As shown in FIG. 4, test device 150 comprises sensor 42, configurable information storage device 160, and input/output pads 48A/48B. Configurable information storage device 160 includes an array 162 of conductive elements 164, connective trace 165 (acting as a conductive element) with first end 166 and second end 168, and input/output pad 169.

In one embodiment, sensor 42 comprises an electrochemical sensor electrode pair 42A/42B configured to perform electrochemical reactions between a blood sample and test reagents within test device 150. Connective trace 152A is a conductive element connecting sensor electrode 42A to input/output pad 48A, while connective trace 152B is a conductive element connecting sensor electrode 42B to input/output pad 48B.

Configurable information storage device 160 is connected in parallel to sensor electrode 42B (and its connecting trace 152B) and is configured for a one-time selection of an impedance among a range of impedances to produce a characteristic impedance between input/output pad 48B and input/output pad 169. This characteristic impedance is indicative of a batch chemistry of the chemical reagents of test device 150. The impedance of information storage device 160 is selected by either activating (or deactivating) one or more of the elements 164 of array 162 near the time of manufacture of test device 150. Upon a meter accessing the selected impedance level from test device 150 via input/output pad 169, the meter is calibrated to test device 150 for the particular characteristics of the chemical reagent on the test strip. This calibration occurs automatically, without any affirmative steps by the consumer, and occurs without the use of a conventional calibration chip or calibration test strip that is separate from test device 150 in use with meter 12.

Each element 164 of array 162 of information storage device 160 comprises a conductive element, such as an inductor, capacitor, or a resistor. Each element 164 is activated or deactivated by physical alteration of a portion of element 164 to cause either a short circuit or an open circuit in that element 164. Upon physical alteration of a select number of elements 164, a characteristic impedance is achieved (between input/output pad 48B and input/output pad 169 for array 162) that is indicative of a property of the chemical reagents of test device 150.

Input/output pad 169 of test device 150, in combination with input/output pads 48A, 48B are configured to communicate with meter 12 that is configured, at input/output pads 78, to read an impedance between input/output pad 169 and input/output pad 48B. Test device 150 also can be used with a conventional meter via input/output pads 48A, 48B, although the conventional meter will not be able to read calibration information on information storage device 160 since conventional meters lack an associated input/output pad for coupling to input/output pad 169 of test device 150.

Figure 5:
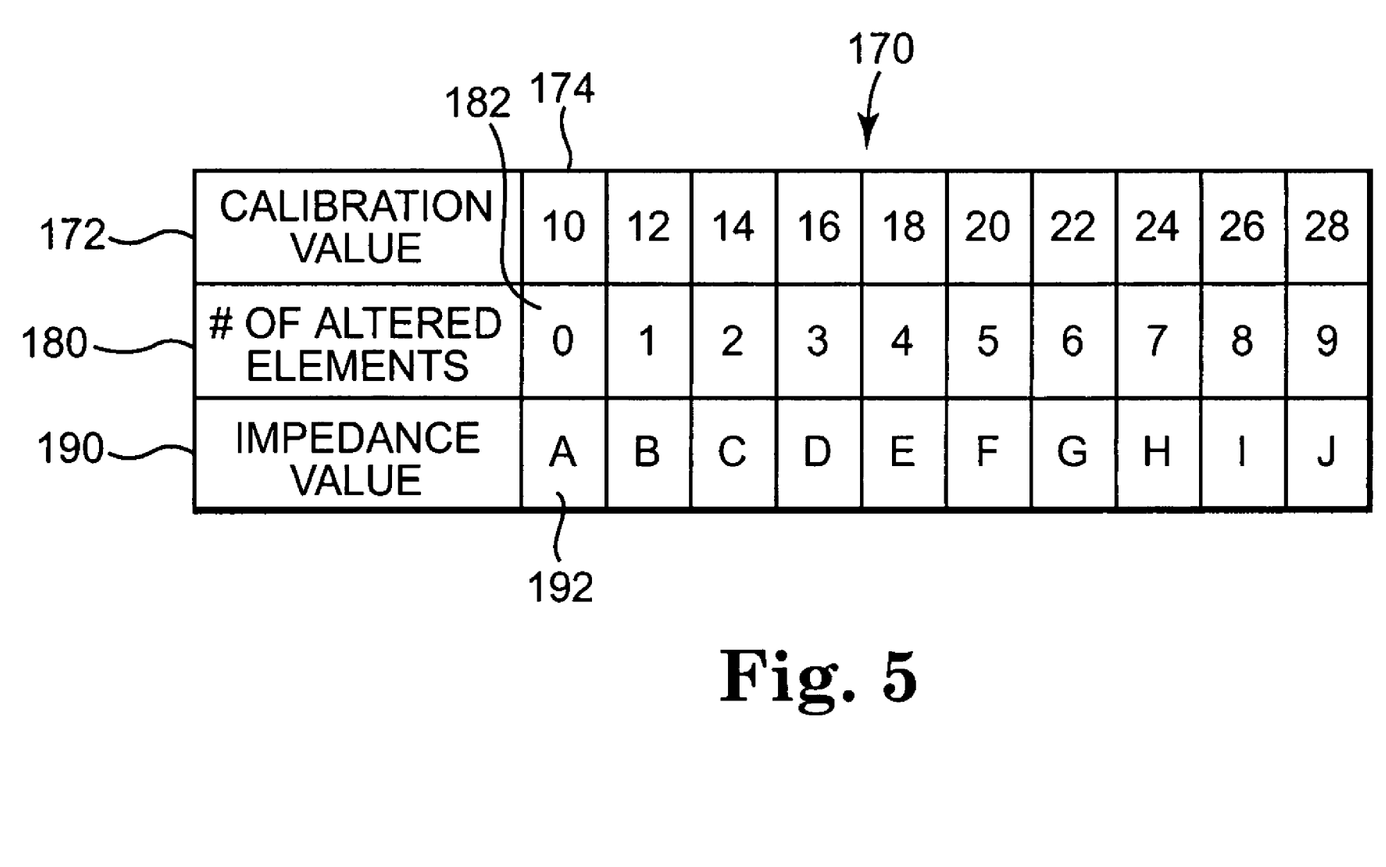
FIG. 5 is a table illustrating parameters of an information storage device, according to an embodiment of the present invention.

FIG. 5 is a table 170 representing a relationship between an information storage device (e.g., information storage device 160 of FIG. 4) and a range of calibration values indicative of a property of a chemical reagent. To determine calibration information to be stored in the information storage device, a range of calibration values is determined that is indicative of a property of the chemical reagents. This range of values is divided into multiple portions (e.g., ten portions) so that a range of impedance values associated with array 162 of conductive elements 164 (FIG. 4) corresponds to the ten portions of the calibration value range. This relationship is illustrated in FIG. 5.

As shown in FIG. 5, calibration table 170 comprises row 172 of calibration values 174, row 180 of the number 182 of altered elements 164, and row 190 of impedance values 192, which corresponds to the calibration values 174 and number 182 of altered elements. The range of calibration values 174 corresponds to a range of quantitatively measurable characteristics of a chemical reagent on test device 150. The number 182 of altered elements shown in table 170 represents the number of conductive elements 164 (FIG. 4) that have been physically altered in information storage device 160. This number 182, in turn corresponds to a calibration value 174 shown in table 170 (e.g., 10, 12, etc.), electrically expressed as an overall impedance value 192 (e.g., A, B, C) shown in table 170 for array 162 of elements 164 within information storage device 160. In some embodiments, these relationships between calibration values and impedance values shown in table 170 also may reflect the order of altered elements. This ordering parameter is suitable for embodiments described in association with FIG. 8, in which the array of physically alterable elements comprises a series of independently addressable fusible links.

As shown in table 170 of FIG. 5, at one end of the calibration range, all of the conductive elements (e.g., inductor(s)) are physically altered while at the other end of the calibration range, none of the conductive elements are physically altered. Intermediate calibration values are obtained by altering only some of the conductive elements. Accordingly, the total number of physically altered conductive elements produces a characteristic impedance for information storage device (e.g., information storage device 160 in FIG. 4) that corresponds to a determined calibration value indicative for a chemical reagent on the test strip.

Finally, in another embodiment wherein the order of altered elements can be inferred or determined, each altered element represents one bit of a binary number from a least significant bit to a most significant bit. Therefore, the number of different calibration values or buckets equals two raised to the power of N wherein N is the number of alterable bits.

Figure 6:
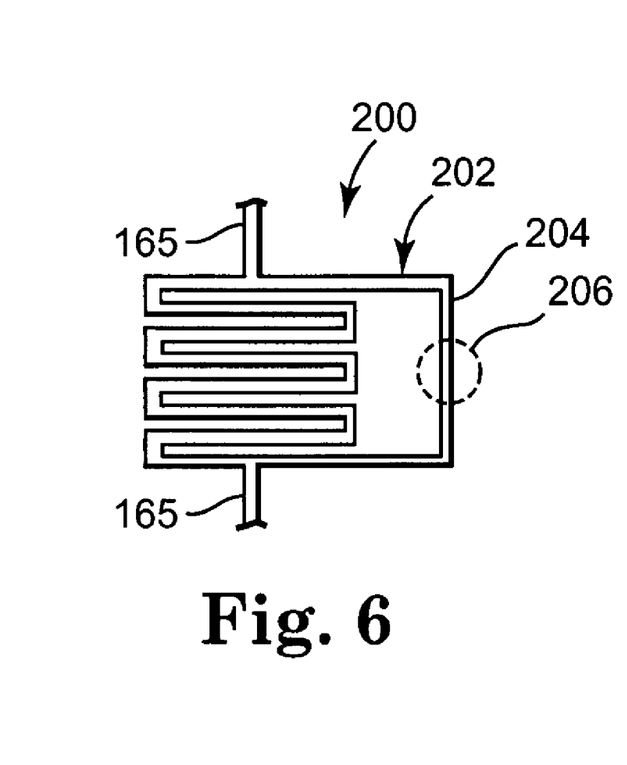
FIG. 6 is plan view schematically illustrating an information storage device, according to an embodiment of the present invention.
Figure 7:
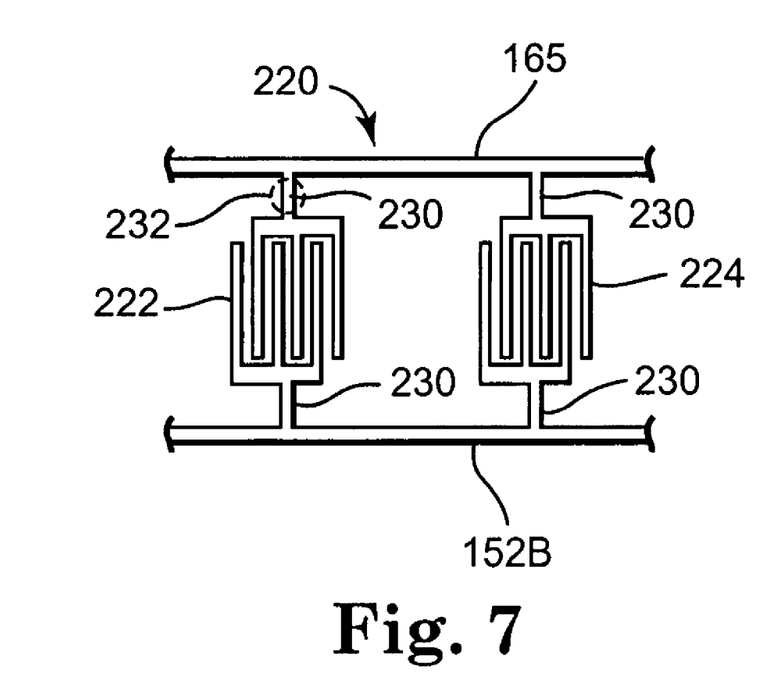
FIG. 7 is plan view schematically illustrating another information storage device, according to an embodiment of the present invention.

Techniques for physically altering conductive elements, as well as various types of conductive elements are described and illustrated in association with FIGS. 6-7.

FIG. 6 illustrates one of the elements 164 of array 162 (FIG. 4) configured as an inductor 200. As shown in FIG. 6, inductor 200 comprises inductive coil 202 with arm 204, and each end of inductor 200 connected to connective trace 165 of information storage device 160. Inductor 200 is deactivated by punching or laser drilling through a portion of the inductor at 206. Inductors 200 of an information storage device are arranged in series (in substantially the same arrangement as shown for elements 164 in FIG. 4), and produce an AC impedance that is determined by the number of inductor elements 164 that are physically altered (see table 170 in FIG. 5). In particular, increasing the number of physically altered inductors 200 as elements 164 produces a higher magnitude inductive impedance for information storage device 160 and consequently between input/output pad 48B and input/output pad 169, which is read by meter 12 (FIGS. 1-2) for calibrating meter 12 to test device 14.

FIG. 7 illustrates one of the elements 164 of array 162 (FIG. 4) configured as a capacitor 220. As shown in FIG. 7, capacitors 222 and 224 each have ends 230 for connecting capacitors 222, 224 in parallel between connective trace 152B of sensor 42 and connective trace 165 of information storage device 160. Capacitor 222 is deactivated by physical alteration at location 232. As previously described in association with FIG. 5, the number of physically altered capacitors 220 as elements 164 determines a characteristic impedance for information storage device 160 that acts as stored calibration information 46 indicative of a property of a chemical reagent on a test strip. This calibration information 46 is read by meter 12 for calibrating meter 12 to test device 14.

Array 162 of elements 164 of information storage device 160 (FIG. 4) can include only one type of impedance element (inductor, capacitor, resistor) or include more than one type, such as a resistor and an inductor. Moreover, impedance elements 164 can be connected in parallel or in series, to achieve a desired range of impedances for using calibration with meter 12 (FIG. 1-2).

In some embodiments, test device 14 is constructed as a substrate with one or more layers of thin film metallization of conductive components such as sensor 42 and configurable information storage device 160 (FIG. 4).

Figure 8:
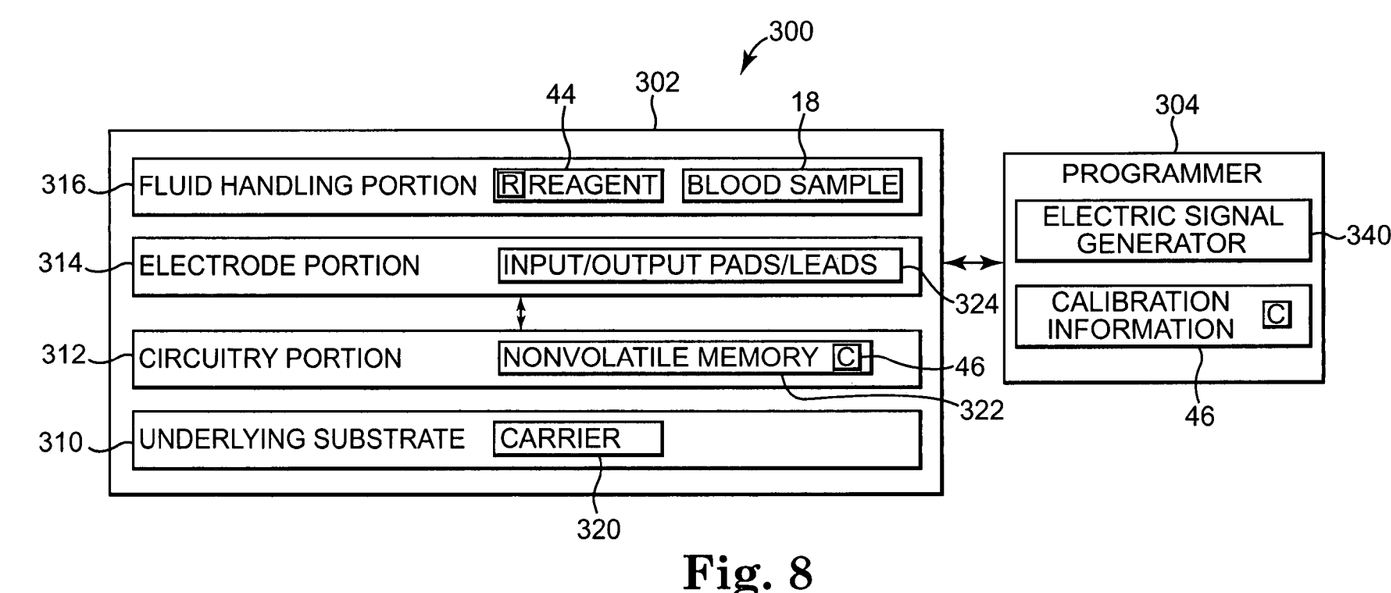
FIG. 8 is a schematic block diagram of another test strip system, according to an embodiment of the present invention.

In other embodiments, test device 14 is constructed using semiconductor microfabrication techniques. For example, FIG. 8 is a schematic view functionally representing a disposable test device made according to microfabrication semiconductor techniques, analogous to technology used in manufacturing flat panel displays. In particular, system 300 comprises test device 302 and programmer 304. Test device 302 comprises a layered arrangement of substrate 310, circuitry portion 312, electrode portion 314, and fluid handling portion 316. Programmer 304 comprises electric signal generator 340 and calibration information (C) 46.

In one embodiment, substrate 310 of test device 302 is constructed from a plastic, glass, or ceramic material and acts as a carrier 320 to the other portions, while circuitry portion 312 is made of an amorphous silicon or polycrystalline silicon material.

Circuitry portion 312 of test strip 302 defines non-volatile memory portion 322 which is configured for storing calibration information (C) 46 (e.g., a value indicative of a property of chemical reagent, date of manufacture, electrode characteristics, etc). Calibration information 46 is written into memory portion 322 via electrical signal generator 340 of programmer 304 and then is retrievable by a meter (e.g., meter 12 in FIGS. 1-2) via input/output pads of electrode portion 314 of test strip 302 that are in electrical communication with memory portion 322 of circuitry portion 312. In one embodiment, circuitry portion 312 comprises thin film transistor (TFT) circuitry. The TFT circuitry includes a portion for addressing a form of the information storage device such as a non-volatile memory.

In one embodiment, the storage device includes a number of fusible links each coupled to independently addressable power transistors. The particular fusible links that are severed during manufacture of test device 302 is indicative of information including the proper calibration information for test device 302. In one embodiment, each fusible link represents a bit of one or more binary numbers that represent the information.

In one embodiment, electrode portion 314 of test device 302 comprises a deposited metallization layer made from conductive trace materials such as copper, gold, platinum, palladium, graphite, etc, for forming a set 324 of electrode pads, input/output pads, connective traces, etc.

Fluid handling portion 316 defines a test surface carrying chemical reagents and is configured for receiving a blood sample for electrochemical reaction with reagents. Fluid handling portion 316 is disposed generally over electrode portion 314 and comprises a plastic, photopolymer, or glass material suitable for that purpose.

In use, test device 302 is constructed and made available for addition of a chemical reagent onto fluid handling portion 316 of test device 302. Once a chemical reagent is added to a set of test devices 302 and a calibration parameter is known that corresponds to particular batch chemistry for that set of test devices 302, then that calibration parameter is electrically sent to all test devices 302 as electrical signal for storage in memory portion 322 of test device 302. In addition, in some embodiments, calibration information represents other or additional parameters such as electrode characteristics, date of manufacture, etc. In this way, each test device 302 stores calibration information (e.g., calibration parameters) electronically within the test device 302 so that calibration parameters are inseparable from the test device 302 that is to be used by the patient.

In an exemplary embodiment, circuitry portion 312 includes a number of power thin film transistors that are each coupled to a fusible link. During manufacture of test device 302, the power thin film transistors are used to selectively burn fusible links to encode information including information indicative of the calibration parameter. The calibration parameter is represented by a binary word, and each bit of that word corresponds to one of the fusible links.

When the device 302 is inserted into meter 12, meter 12 retrieves electronically stored calibration parameters from memory portion 322 of test device 302 via input/output pads to calibrate meter 12 to test device 302. This calibration occurs automatically and transparently to the user, independent of and without any separate manually entered calibration code, separate calibration memory chip, optical calibration code/color, or separate calibration test strip (i.e., a test strip used solely for calibration). This can be done by using the power thin film transistors to couple the fusible links to circuitry for decoding the binary word.

Embodiments of the present invention enable highly accurate calibration of disposable analyte test devices with meters by effectively sidestepping user interaction in calibrating the meter. In particular, calibration information is electronically stored in each test device so that no separate calibration chip, alphanumeric key-entered calibration code, optical calibration code, etc is required for calibrating a meter to the test device. Moreover, the calibration information is inseparable from the test strip, as circuitry defining an information storage device (that stores the calibration information) is formed directly on or within the disposable test device. With the calibration information stored in each test device at or near the time of manufacture, for example, when the chemical reagents are placed on the test devices, potential calibration errors are further minimized. Although specific embodiments have been illustrated and described herein, it will be appreciated by those of ordinary skill in the art that a variety of alternate and/or equivalent implementations may be substituted for the specific embodiments shown and described without departing from the scope of the present invention. This application is intended to cover any adaptations or variations of the specific embodiments discussed herein. Therefore, it is intended that this invention be limited only by the claims and the equivalents thereof.

What is claimed is:

1. A self-calibrating, disposable blood test device insertable in a meter, the test device comprising:
   a substrate configured for carrying a chemical reagent; and
   circuitry formed on the substrate, the circuitry comprising:
      a sensor portion associated with the chemical reagent to enable measurement of at least one of a presence and a concentration of a blood analyte, the sensor portion including an electrode sensor;
      an input/output pad connected to the electrode sensor; and
      an additional input/output pad connected to an information storage portion that is connected in parallel with the electrode sensor;
      wherein the information storage portion is configured to store information indicative of a property of the chemical reagent for calibration of the meter, the information storage portion including a plurality of impedance elements including at least one of: a plurality of inductors arranged in series; or a plurality of capacitors arranged in parallel, wherein each impedance element includes a region that may be physically altered by at least one of punching, drilling, or shorting via fusible link, to create a short circuit or open circuit, in order to activate or deactivate the impedance element
   wherein the information is stored by activating or deactivating a select number of the impedance elements in a determinable order, which creates a characteristic impedance between the input/output pad and the additional input/output pad that is measurable by the meter and which corresponds to at least one calibration value that is indicative of the property of the chemical reagent;
   and wherein the impedance elements within the information storage portion are arranged such that $2^N$ different potential characteristic impedances may be produced, wherein N is the number of impedance elements.

2. The test device of claim 1, wherein the test device comprises one of a set of test devices with the information storage portion of each test device storing substantially the same information in the information storage portion to be indicative of the at least one calibration value of the chemical reagent for the set of test devices.

3. The test device of claim 1, wherein the circuitry of the substrate comprises a semiconductor portion and the circuitry defines a non-volatile memory configured to store the information.

4. The test device of claim 3, further comprising an electrical signal generator external to the test device and configured to send an electrical signal to the non-volatile memory to cause storage of the information in the information storage portion of the test device.

5. The test device of claim 3, wherein the non-volatile memory is configured to also store at least one of a date of manufacture, an operating characteristic, and serial number.

6. A method of manufacturing a test device insertable in a meter for the detection of a blood analyte, the method comprising:
   forming circuitry on a substrate of the test device, the substrate configured for carrying a chemical reagent, and the circuitry including:
      a sensor portion associated with the chemical reagent to enable measurement of at least one of a presence and a concentration of a blood analyte, the sensor portion including an electrode sensor;
      an input/output pad connected to the electrode sensor; and
      an additional input/output pad connected to an information storage portion that is connected in parallel with the electrode sensor;
      wherein the information storage portion is configured to store information indicative of a property of the chemical reagent for calibration of the meter, the information storage portion including a plurality of impedance elements including at least one of: a plurality of inductors arranged in series; or a plurality of capacitors arranged in parallel, wherein each impedance element includes a region that may be physically altered by at least one of punching, drilling, or shorting via fusible link, to create a short circuit or open circuit, in order to activate or deactivate the impedance element
   depositing the chemical reagent on the sensor portion that enables detection of the blood analyte; and
   storing information in the information storage portion;
   wherein the information is stored by activating or deactivating a select number of the impedance elements in a determinable order, which creates a characteristic impedance between the input/output pad and the additional input/output pad that is measurable by the meter and which corresponds to at least one calibration value that is indicative of the property of the chemical reagent;
   and wherein the impedance elements within the information storage portion are arranged such that $2^N$ different potential characteristic impedances may be produced, wherein N is the number of impedance elements.

7. The method of claim 6, further comprising:
   determining a property of the test device, the property of the test device being selected from the at least one calibration value of the chemical reagent, a date of manufacture, an analyte array identifier, and an operating characteristic.

8. The method of claim 7, wherein storing information in the information storage portion comprises storing at least one of the at least one calibration value of the chemical reagent, the date of manufacture, the analyte array identifier, and the operating characteristic.

9. The method of claim 6, wherein forming the information storage portion of the circuitry comprises forming a thin film circuitry portion on the substrate that defines a non-volatile memory portion, and wherein storing information in the information storage portion comprises sending an electrical signal to the information storage portion to store a value in the non-volatile memory portion.

10. The method of claim 6, further comprising:
    measuring the at least one calibration value of the chemical reagent to determine a calibration factor for the test device;
    wherein storing information in the information storage portion comprises altering at least one of the plurality of impedance elements, wherein the number of altered impedance elements is indicative of the calibration factor of the test device.

11. The method of claim 10, wherein altering the plurality of impedance elements comprises disabling at least one of the plurality of impedance elements by at least one of physically removing a conductive portion of the impedance element and physically adding a conductive portion to the impedance element.

12. The test strip of claim 1, wherein the information storage portion is inseparable from the disposable test strip.

13. The test device of claim 1 wherein:
the electrode sensor includes first and second electrode sensors;
the input/output pad includes:
  a first input/output pad connected to the first electrode sensor; and
  a second input/output pad connected to the second electrode sensor; and
the characteristic impedance is created between the second input/output pad and the additional input/output pad.

* * * * *